United States Patent [19]

Möhring et al.

[11] 4,174,445

[45] Nov. 13, 1979

[54] PREPARATION OF ARTHROPODICIDALLY ACTIVE SUBSTITUTED TRIAZINE-2,4-DIONES

[75] Inventors: Edgar Möhring; Peter Roessler, both of Bergisch Gladbach, Fed. Rep. of Germany

[73] Assignee: Bayer Aktiengesellschaft, Leverkusen, Fed. Rep. of Germany

[21] Appl. No.: 839,694

[22] Filed: Oct. 5, 1977

[30] Foreign Application Priority Data

Oct. 23, 1976 [DE] Fed. Rep. of Germany ....... 2648120
May 23, 1977 [DE] Fed. Rep. of Germany ....... 2723119

[51] Int. Cl.² .......................................... C07D 251/16
[52] U.S. Cl. ..................................... 544/223; 424/249
[58] Field of Search ......................... 544/223; 424/249

[56] References Cited

U.S. PATENT DOCUMENTS

| 3,873,540 | 3/1975 | Fuchs et al. | 544/223 |
| 3,933,815 | 1/1976 | Ploeg | 544/223 |
| 3,951,971 | 4/1976 | Fuchs et al. | 544/223 |
| 4,048,315 | 9/1977 | Bredereck et al. | 544/223 |
| 4,056,527 | 11/1977 | Schlee et al. | 544/223 |

*Primary Examiner*—John M. Ford
*Attorney, Agent, or Firm*—Sprung, Felfe, Horn, Lynch & Kramer

[57] ABSTRACT

Substituted triazine-2,4-diones of the formula

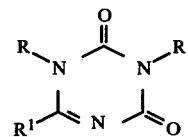

in which
R is an organo radical, and
R¹ is hydrogen or an organo radical, which possess arthropodicidal properties and are produced by reacting an isocyanate of the formula

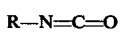

R—N=C=O with a bis-silylated carboxylic acid amide of the formula

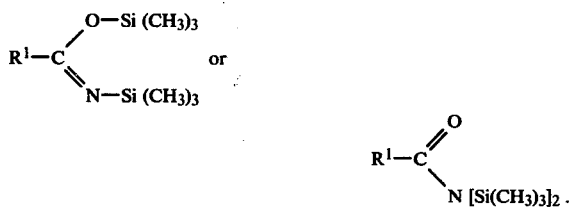

9 Claims, No Drawings

PREPARATION OF ARTHROPODICIDALLY ACTIVE SUBSTITUTED TRIAZINE-2,4-DIONES

The present invention relates to and has for its objects the provision of particular new substituted triazine-2,4-diones which possess arthropodicidal properties, active compositions in the form of mixtures of such compounds with solid and liquid dispersible carrier vehicles, and methods for producing such compounds and for using such compounds in a new way especially for combating pests, e.g. arthropods, with other and further objects becoming apparent from a study of the within specification and accompanying examples.

It has already been disclosed that the reaction of urea with triethyl orthoformate produces unsubstituted symmetrical triazine-2,4-dione (H. Bredereck, F. Effenberger and A. Hofmann, Angew, Chemie, volume 74, page 354 (1962)). However, only unsubstituted triazine-2,4-diones are producible by this process.

Furthermore, it has been disclosed that 1,3-disubstituted symmetrical triazine-2,4-diones are produced by the reaction of correspondingly substituted biurets with triethyl orthoformate (A. Piskala and J. Gut, Chemical Abstracts, volume 56, 4766 b). However, this process is restricted to the preparation of the 1,3-disubstituted triazine-2,4-diones and is thus not universally applicable.

It has also been disclosed to prepare 1,3,6-trimethyl-triazine-2,4-dione by alkylating 6-methyl-triazine-2,4-dione by means of dimethyl sulphate (G. Ostrogovich and M. Safta, Chemical Abstracts, volume 78, 84,396 y). However, in this process, 6-methyl-triazine-2,4-dione must first be prepared as a starting material, which is alkylated in a second stage. This process is unsatisfactory in respect of its overall yield and is unsuitable for commercial implementation.

Further, it has been disclosed that 1,3-dimethyltriazine-2,4-dione is produced by thermal rearrangement from 2,4-dimethoxy-1,3,5-triazine (A. Piskala and J. Gut, Chemical Abstracts, volume 62, 624 g). However, the yield of this reaction, which takes place at 220° C., is also unsatisfactory since numerous by-products are formed. Furthermore, the reaction is restricted to the stated compound and does not permit the broad preparation of other substituted triazine-2,4-diones. This process is thus also not suitable for the commercial preparation of substituted triazine-2,4-diones.

The present invention now provides, as new compounds, the substituted triazine-2,4-diones of the general formula

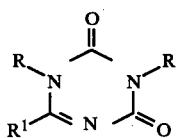

(I), in which
R represents alkyl with up to 20 carbon atoms carrying one or more substituents selected from the group consisting of halogen, CN, aryloxy especially optionally substituted phenoxy, alkoxy, halogenalkoxy, alkylmercapto, halogenalkylmercapto or represents furthermore phenyl carrying one or more substituents selected from the group consisting of halogenoalkyl, optionally halogen-substituted phenoxy, alkoxy, halogenoalkoxy, alkylmercapto, alkoxycarbonylalkenyl and halogenoalkylmercapto radicals and which can optionally be further substituted by halogen, or represents phenylsulphonyl which is optionally substituted by halogen, nitro, CN, monoalkylamino, dialkylamino, alkylmercapto or alkoxy, or represents alkylsulphonyl which is optionally substituted by halogen or CN, and $R^1$ represents hydrogen or alkyl with 1–10 carbon atoms or cycloalkyl with 5–10 carbon atoms, either of which is optionally substituted by halogen, alkoxy, cyano or nitro, or represents phenyl or naphthyl which are optionally substituted by halogen, nitro, cyano, alkyl with 1–10 carbon atoms, halogenoalkyl, alkoxy or alkylmercapto.

It was surprising that the compounds obtainable in accordance with the process of the invention exhibit an excellent development-inhibiting activity, since such an action was not known from the known compounds of this type. All that was known was that 1,3-dimethyltriazine-2,4-dione possesses a certain bactericidal activity.

Unless otherwise recited, the various alkyl moieties advantageously contain from 1 to 4 carbon atoms.

Preferably, R represents phenyl carrying one or more substituents selected from the group of trihalogenomethyl, ethoxy, ethoxycarbonylvinyl, phenoxy and halogenophenoxy radicals and which can optionally be further substituted by chlorine. Furthermore, R represents preferably alkyl substituted by halogen, especially chlorine. $R^1$ represents hydrogen, methyl, ethyl, n-propyl, isopropyl, cyclohexyl or phenyl.

The present invention also provides a process for the preparation of a compound of the formula (I) in which a bis-silylated carboxylic acid amide of the general formula

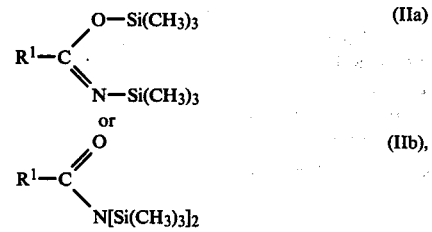

in which
$R^1$ has the above-mentioned meaning, is reacted with an isocyanate of the general formula

R—N=C=O         (III), in which
R has the above-mentioned meaning, if appropriate in the presence of a diluent.

The reaction of bis-silylated carboxylic acid amides with isocyanates is new and gives new substituted triazine-2,4-diones. It was surprising and not foreseeable that the hitherto not previously obtained substituted triazine-2,4-diones could be prepared by this reaction in such a simple manner and in high yield. The process is distinguished by the choice of relatively simple starting compounds which are readily available and easily handled. It permits both the preparation of 1,3-disubstituted triazine-2,4-diones and the preparation of 1,3,6-trisubstituted triazine-2,4-diones. In contrast, the known processes for the preparation of compounds of this type permit either only the preparation of the corresponding 1,3-disubstituted compounds or only the preparation of the 1,3,6-trimethyl-substituted compound.

If bis-trimethylsilylformamide and phenyl isocyanate are used as starting components, the course of the reaction can be represented by the following equation:

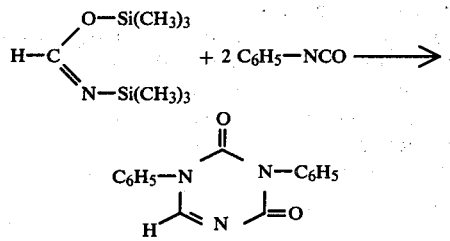

The structure of bis-trimethyl-silylformamide has not yet been clarified unambiguously. It is conceivable that this compound is also present as N,N-bis-trimethylsilylformamide, and formula (II) should be interpreted accordingly.

The particularly preferred starting compound of the general formula (II) is bis-trimethylsilylformamide. Some of the compounds of the general formula (II) are known (J. F. Klebe et al., J. Amer. Chem. Soc., 88/14, 3390, 1966, and French Pat. No. 1,442,585). The other compounds (II) can be prepared by analogous methods.

Preferred starting compounds of the general formula (III) are 4-trifluoromethylphenyl isocyanate, 4-trifluoromethyl-3-chlorophenyl isocyanate and 4'-chlorophenoxy-4-phenyl isocyanate and chlorohexyl isocyanate.

The reaction according to the invention is preferably carried out in the presence of an inert organic diluent (which term herein includes a solvent). As such, it is possible to use aliphatic, aromatic and optionally chlorinated hydrocarbons, for example benzene, toluene, xylene, benzine, methylene chloride, chloroform, carbon tetrachloride and chlorobenzene; ethers, such as diethyl ether, dibutyl ether and dioxane; ketones, such as acetone, methyl ethyl ketone, ethyl isopropyl ketone and methyl isobutyl ketone; and nitriles, such as acetonitrile.

The reaction can be carried out under normal pressure.

The reaction temperature can vary within a wide range. In general, the reaction is carried out at about 10° to 150° C., preferably about 35° to 100° C.

In general, the starting materials are employed in stoichiometric amounts.

The active compounds are well tolerated by plants, have a favorable level of toxicity to warm-blooded animals, and can be used for combating arthropod pests, especially insects and arachnids, and nematodes which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus*, *Armadillidium vulgare* and *Porcellio scaber*;

from the class of the Diplopoda, for example *Blaniulus guttulatus*;

from the class of the Chilopoda, for example *Geophilus carpophagus* and Scutigera spec.;

from the class of the Symphyla, for example *Scutigerella immaculata*;

from the order of the Thysanura, for example *Lepisma saccharina*;

from the order of the Collembola, for example *Onychiurus armatus*;

from the order of the Orthoptera, for example *Blatta orientalis*, *Periplaneta americana*, *Leucophaea maderae*, *Blattella germanica*, *Acheta domesticus*, Gryllotalpa spp., *Locusta migratoria migratorioides*, *Melanoplus differentialis* and *Schistocerca gregaria*;

from the order of the Dermaptera, for example *Forficula auricularia*;

from the order of the Isoptera, for example Reticulitermes spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci*;

from the order of the Heteroptera, for example Eurygaster spp., *Dysdercus intermedius*, *Piesma quadrata*, *Cimex lectularius*, *Rhodnius prolixus* and Triatoma spp.;

from the order of the Homoptera, for example *Aleurodes brassicae*, *Bemisia tabaci*, *Trialeurodes vaporariorum*, *Aphis gossypii*, *Brevicoryne brassicae*, *Cryptomyzus ribis*, *Doralis fabae*, *Doralis pomi*, *Eriosoma lanigerum*, *Hyalopterus arundinis*, *Macrosiphum avenae*, Myzus spp., *Phorodon humuli*, *Rhopalosiphum padi*, Empoasca spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, Pseudococcus spp. and Psylla spp.;

from the order of the Lepidoptera, for example *Pectinophora gossypiella*, *Bupalus piniarius*, *Cheimatobia brumata*, *Lithocolletis blancardella*, *Hyponomeuta padella*, *Plutella maculipennis*, *Malacosoma neustria*, *Euproctis chrysorrhoea*, Lymantria spp., *Bucculatrix thurberiella*, *Phyllocnistis citrella*, Agrotis spp., Euxoa spp., Feltia spp., *Earias insulana*, Heliothis spp., *Laphygma exigua*, *Mamestra brassicae*, *Panolis flammea*, *Prodenia litura*, Spodoptera spp., *Trichoplusia ni*, *Carpocapsa pomonella*, Pieris spp., Chilo spp., *Pyrausta nubilalis*, *Ephestia kuehniella*, *Galleria mellonella*, *Cacoecia podana*, *Capua reticulana*, *Choristoneura fumiferana*, *Clysia ambiguella*, *Homona magnanima* and *Tortrix viridana*;

from the order of the Coleoptera, for example *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, Diabrotica spp., *Psylliodes chrysocephala*, *Epilachna varivestis*, Atomaria spp., *Oryzaephilus surinamensis*, Anthonomus spp., Sitophilus spp., *Otiorrhynchus sulcatus*, *Cosmopolites sordidus*, *Ceuthorrhynchus assimilis*, *Hypera postica*, Dermestes spp., Trogoderma spp., Anthrenus spp., Attagenus spp., Lyctus spp., *Meligethes aeneus*, Ptinus spp., *Niptus hololeucus*, *Gibbium psylloides*, Tribolium spp., *Tenebrio molitor*, Agriotes spp., Conoderus spp., *Melolontha melolontha*, *Amphimallon solstitialis* and *Costelytra zealandica*;

from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata,* Dacus oleae and Tipula paludosa;

from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g., acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawduct, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

The active compounds according to the invention can, depending on the intended use, be combined with other insecticidally active compounds to intensify and supplement their spectrum of action. In particular, the active compounds mentioned below, and other representatives of the groups of active compounds characterized by these active compounds, are suitable for this purpose.

Organic phosphorus compounds, such as O,O-dimethyl-S-isopropyl-2-sulphinylethylthiophosphate=O,O-dimethyl-S-(2-methoxyethyl-acetamide)-dithiophosphate (Medithionat) O,O-diethyl-S-(N-ethoxycarbonyl-N-methylcarbamoylmethyl)-dithiophosphate (Mecarbam), S-(5-methoxy-4-pyron-2-yl-methyl)-O,O-dimethylthiophosphate O,S-dimethyl-N-acetyl-amido-thiophosphate (Acetphate), 1-phenyl-3-(diethoxy-thiophosphoryloxy)-1,2,4-triazole (Triazophos), O,O-diethyl-O-[6-(3-(2-phenyl)-pyridazinonyl)]-thiophosphate 4-(dimethoxy-thiophosphoryloxy)-2-diethylamino-6-methyl-pyrimidine (Pirimiphos-Methyl), 4-diethoxythiophosphoryloxy)-2-diethylamino-6-methyl-pyrimidine (Pirimiphos-Ethyl), O,O-diethyl-O-(3- chloro-7-methyl-2-pyrazolo[1,5-α]pyrimidinyl)-thiophosphate (Chlorpyrophos), O-ethyl-S-n-propyl-O-(2,4-dichlorophenyl)thiophosphate (Dichlorpropafos), O-ethyl-O(4-methylmercaptophenyl)-S-n-propyldithiophosphate (Mercapto-propafos), O-ethyl-O-(2-carbisopropoxyphenyl)-isopropyl-amidothiophosphate (Isofenphos), S-chloromethyl-diethyl-phosphorthiolothionate (Chlormephos), S-(tert.-butylthio)methyl-O,O-diethyldithiophosphate, O,O-diethyl-O-[O-chlorophenyl-O-glyoxylonitrile-oxime]-thiophosphate (Chlorphoxim), O,O-diethyl-O-phenylglyoxylonitrile-oxime-thiophosphate (Methylphoxim), bis-O,O-diethyl-phosphoric acid anhydride (TEPP), dimethyl(2,2,2-trichloro-1-hydroxyethyl)phosphonate (Trichlorfon), 1,2-dibromo-2,2-dichloroethyl-dimethylphosphate (Naled), 2,2-dichlorovinyl-dimethylphosphate (Dichlorvos), 2-methoxycarbamyl-1-methylvinyldimethylphosphate (Mevinphos), dimethyl-1-methyl-2-(methylcarbamoyl)-vinylphosphate cis (Monocrotophos), 3-dimethoxyphosphinyloxy)-N,N-dimethyl-cis-crotonamide (Dicrotophos), 2-chloro-3-diethylcarbamoyl-1-methyl-vinyldimethylphosphate (Phosphamidon), O,O-diethyl-O(or S)-2-(ethylthio)-ethylthiophosphate (Demeton), S-ethylthioethyl-O,O-dimethyl-dithiophosphate (Thiometon), O,O-diethyl-S-ethylmercaptomethyldithiophosphate (Phorate), O,O-diethyl-S-2-ethylthioethyl-dithiophosphate (Disulfoton), O,O-dimethyl-S-2(ethylsulphinyl)ethylthiophosphate (Oxydemeton-methyl), O,O-dimethyl-S-(1,2-dicarbethoxyethyl-dithiophosphate (Malathion), O,O,O,O-tetraethyl-S,S'-methylene-bis-dithiophosphate (Ethion), O-ethyl-S,S-dipropyldithiophosphate (Prophos), O,O-dimethyl-S-(n-methyl-N-formylcarbamoylmethyl)-dithiophosphate (Formothion), O,O-dimethyl-S-(N-methylcarbamoylmethyl)-dithiophosphate (Dimethoate), O,O-dimethyl-O-p-nitrophenyl-thiophosphate (Parathion-methyl), O,O-diethyl-O-p-nitrophenyl-thiophosphate (Parathion), O-ethyl-O-p-nitrophenylphenylthiophosphonate (EPN), O,O-dimethyl-O-(4-nitro-m-tolyl)thiophosphate (Fenitrothion), O,O-dimethyl-O-2,4,5-trichlorophenyl-thiophosphate (Ronnel), O-ethyl-O-2,4,5-trichlorophenylethylthiophosphonate (Trichloronate), O,O-dimethyl-O-2,5-dichloro-4-bromophenylthiophosphate (Bromophos), O,O-dimethyl-O-(2,5-dichloro-4-iodophenyl)-thiophosphate (Iodofenphos), 4-tert.-butyl-2-chlorophenyl-N-methyl-O-methylamidophosphate (Crufomat), O,O-dimethyl-O-3-(3-methyl-4-methylmercaptophenyl)thiophosphate (Fenthion), isopropylamino-O-ethyl-O-(4-methylmercapto-3-methyl-phenyl)-phosphate (Phenamiphos), O,O-diethyl-O-p-(methylsulphoninyl)-phenyl-thiophosphate (Fensulfothion), O-p-(dimethylsulphamido)-phenyl-O,O-dimethylthiophosphate (Famphur), O,O,O',O'-tetramethyl-O,O'-thiodi-p-phenylenethiophosphate, O-ethyl-S-phenylethyldithiophosphonate (Fonofos), O,O-dimethyl-O-(α-methylbenzyl-3-hydroxycrotonyl)-phosphate, 2-chloro-1-(2,4-dichlorophenyl)-vinyl-diethylphosphate (Chlorfenvinphos), 2-chloro-1-(2,4,5-trichlorophenyl)-vinyl-dimethylphosphate, O-[2-chloro-1-(2,5-dichlorophenyl)]-vinyl-O,O-diethylthiophosphate, phenylglyoxylonitrile-oxime-O,O-diethylthiophosphate (Phoxim), O,O-diethyl-O-(3-chloro-4-methyl-2-oxo-2H-1-benzopyran-7-yl)-thiophosphate (Coumaphos), 2,3-p-dioxanedithiol-S,S-bis(O,O-diethyldithiophosphate) (Dioxathion), 5-[(6-chloro-2-oxo-3-benzoxazolinyl)methyl]-O,O-diethyldithiophosphate (Phosalon), 2-(diethoxy-phosphinylimino)-1,3-dithiolane (Phosfolan), O,O-dimethyl-S-[2-methoxy-1,3,4-thiadiazol-5-(4H)-onyl-(4)-methyl]dithiophosphate (Methidathion), O,O-dimethyl-S-phthalimidoethyl-dithiophosphate (Imidan), O,O-diethyl-O-(3,5,6-trichloro-2-pyridyl)thiophosphate (Chlorpyrifos), O,O-diethyl-O-2-pyrazinyl-thiophosphate (Thionazin), O,O-diethyl-O-(2-isopropyl-4-methyl-6-pyrimidyl)thiophosphate (Diazinon), O,O-diethyl-O-(2-quinoxalyl)-thiophosphate (Quinalphos), O,O-dimethyl-S-(4-oxo-)-2,3-benzotriazin-3(4H)-yl-methyl)-dithiophosphate (Azinphosmethyl), O,O-diethyl-S-(4-oxo-1,2,3-benzotriazin-3(4H)-yl-methyl)-dithiophosphate (Azinphosethyl), S-[(4,6-diamino-s-triazin-2-yl)methyl]-O,O-dimethyldithiophosphate (Menazon), O,O-dimethyl-O-(3-chloro-4-nitrophenyl)thiophosphate (Chlorthion), O,O-dimethyl-O(or S)-2-(ethylthioethyl)thiophosphate (Demeton-S-Methyl), 2-(O,O-dimethyl-phosphoryl-thiomethyl)-5-methoxypyrone-4-3,4-dichlorobenzyl-triphenylphosphonium chloride, O,O-diethyl-S-(2,5-dichlorophenyl-thiomethyl) dithiophosphate (Phenkapton), 5-azino-bis(dimethylamido)phosphinyl-3-phenyl-1,2,4-triazole (Triamiphos), N-methyl-5-(O,O-dimethylthiolphosphoryl)-3-thiavaleramide (Vamidothion), O,O-dimethyl-S-(methylcarbamoylmethyl)-thiophosphate (Omethoat), O-ethyl-O-(8-quinolinyl)-phenylthiophosphonate (Oxinothiophos), O-methyl-S-methyl-amido-thiophosphate (Methamidophos), O-methyl-O-(2,5-dichloro-4-bromophenyl)-benzothiophosphonate (Phosvel), O,O-diethyl-S-(N-isopropylcarbamoylmethyl)-dithiophosphate (Prothoat), S-N-(1-cyano-1-methylethyl)carbamoylmethyldiethylthiolphosphate (Cyanthoat), S-(2-acetamidoethyl)-O,O-dimethyldithiophosphate, O,O-dimethyl-O-(2-chloro-4-nitrophenyl) thiophosphate (Dicapthon), O,O-dimethyl-O-p-cyanophenylthiophosphate (Cyanox), O-ethyl-O-p-cyanophenyl-thiophosphonate, O,O-diethyl-0,2,4-dichlorophenylthiophosphate (Dichlorfenthion), O,O-diethyl-O-2,5-dichloro-4-bromophenylthiophosphate (Bromophos-ethyl), dimethyl-p-(methylthio)-phenylphosphate, O,O-dimethyl-O-p-sulphamidophenylthiophosphate, O-[p(p-chlorophenyl)azophenyl]O,O-dimethylthiophosphate (Azothoat), O,O-dimethyl-S-p-chlorophenylthiophosphate, O,O-dimethyl-S-(p-chlorophenylthiomethyl)dithiophosphate (Methylcarbophenothion), O,O-diethyl-p-chlorophenylmercaptomethyl-dithiophosphate (Carbophenothion), O,O-diethyl-S-p-chlorophenylthiomethyl-thiophosphate, O,O-dimethyl-S-(carbethoxy-phenylmethyl)dithiophosphate (Phenthoat), O,O-diethyl-7-hydroxy-3,4-tetramethylenecoumarinyl-thiophosphate (Coumithoat), 2-methoxy-4-H-1,3,2-benzodioxaphosphorine-2-sulphide, S-(2-chloro-1-phthalimidoethyl)-O,O-diethyldithiophosphate (Dialiflor), N-hydroxynaphthalimido-diethylphosphate, O,O-dimethyl-O-(3,5,6-trichloro-2-pyridyl)thiophosphate, S-2-(ethylsulphonyl)ethyl-dimethylthiolphosphate (Dioxydemeton-S-Methyl), diethyl-S-2-(ethylsulphinyl)ethyl-dithiophosphate (Oxydisulfoton), bis-O,O-diethylthiophosphoric acid anhydride (Sulfotep), dimethyl-1,3-di(carbomethoxy)-1-propen-2-yl-phosphate, dimethyl-(2,2,2-trichloro-1-butyroyloxyethyl)phosphonate (Butonat), dimethyl-N-methoxymethylcarbamoylmethyl-dithiophosphate (Formocarbam), O-ethyl-S,S-diphenyldithiolphosphate (Ediphenphos), diisopropylaminofluorophosphate (Mipafox), O,O-dimethyl-S-(morpholinylcarbamoylmethyl)dithiophosphate (Morphothion), octamethylpyrophosphoramide (Schradan), N,N,N',N'-tetramethyldiamidofluorophosphate (Dimefox), O-methyl-O-(2-carboisopropoxyphenyl)-amidothiophosphate (Isocarbophos), as well as nitrophenols and their derivatives, such as the Na salt of 4,6-dinitro 6-methylphenol [dinitrocresol], the 2,2′,2″-triethanolamine salt of dinitrobutylphenol, 2-(1-methylheptyl)-4,6-dinitrophenyl crotonate [Dinocap], 2-sec.-butyl-4,6-dinitrophenyl 3-methyl-buteneoate [Binapacryl], 2-sec.-butyl-4,6-dinitrophenyl isopropyl-carbonate [Dinobuton] and also dichlorodiphenyltrichloroethane (DDT), 2,2-bis-(p-chlorophenyl)-1,1-dichloroethane (TDE), bis-(p-chlorophenyl)-trichloroethanol (Dicofol), ethyl 4,4′-dichlorodiphenylglycolate (Chlorbenzilate), isopropyl 4,4′-dichlorobenzilate (Chloropropylate), isopropyl 4,4′-dibromobenzilate (Phenisobromolate), 1,1,1-trichloro-2,2-bis-(p-methoxyphenyl)ethane (Methoxychlor), 1,1-bis-(p-ethylphenyl)-2,2-dichloroethane (Perthane), bis-(4-chlorophenyl)-cyclopropylcarbinole (Kilacar), dichlorophenyl benzenesulphonate (Genite), 4-chlorophenyl-2,4,5-trichlorophenyl-azo-sulphide (Milbex), 2-(p-tert.-butylphenoxy)isopropyl 2′-chloroethyl sulphite (Aracide), 2-)p-tert.butylphenoxy)-cyclohexyl 2-propinyl sulphite (Omite), 2-fluoro-N-methyl-N-1-naphthylacetamide (Nissol), N-dichlorofluoromethylthio-dimethylaminosulphonic acid anilide (Dichlofluanid), N-[(dichlorofluoromethyl)-thiol]-N′,N′-dimethyl-N-p-tolylsulphamide (Tolylfluanid), 1,2-dibromo-3-chloropropane (DBCP), 1,5-bis-(2,4-dimethylphenyl)-3-methyl-1,3,5-triazapenta-1,4-diene (Amitraz), ethyl-O-benzoyl-3-chloro-2,6-dimethoxybenzohydroximate (Benzomate), tricyclohexyl-tin hydroxide (Plictran), 1-tricyclohexylstannyl-1,2,4-triazole (Tricyclazol), Torque (Neostanox), isopropyl-11-methoxy-3,7,11-trimethyldodeca-2,4-dienoate (Altosid), ethyl-3,7-11-trimethyl-2,4-dodecadienoate (Altozar), 2,2,2-trichloro-1-(3,4-dichlorophenyl) ethanol acetate (Dichlorofenat), pyrethrin I, pyrethrin IX, 3-allyl-2-methyl-4-oxo-2-cyclopenten-1-yl chrysanthemumate (Allethrin), 6-chloroiperonyl crysanthemumate (Barthrin), 2,4-dimethylbenzyl chrysanthemumate (Dimethtrin), 2,3,4,5-tetrahydrophthalimidomethyl chrysanthemumate, 6-methyl-2-oxo-1,3-dithiolo-[4,5-b]-quinoxaline (Quinomethionat), (1)-3-(2-furfuryl)-2-methyl-4-oxocyclopent-2-enyl(1)-(cis+trans) chrysanthemum-monocarboxylate (Furethrin), 4-chlorobenzyl-4-fluorophenyl-sulphide (Fluorobenside), 5,6-dichloro-1-phenoxycarbanyl-2-trifluoromethyl-benzimidazole (Fenozaflor), p-chlorophenyl-p-chlorobenzenesulphonate (Ovex), p-chlorophenyl-benzenesulphonate (Fenson), p-chlorophenyl-2,4,5-trichlorophenylsulphone (Tetradifon), p-chlorophenyl-2,4,5-trichlorophenyl-sulphide (Tetrasul), p-chlorobenzyl-p-chlorophenyl-sulphide (Chlorbenzide), 2-thio-1,3-dithiolo(5,6)quinoxaline (Thiochinox), prop-2-ynyl-(4-1-butylphenoxy)-cyclohexyl sulphite (Propargil), 1-dimethyl-2-(2′-methyl-4′-chlorophenyl)-formamidine (Chlorphenamidin), and also ureas, such as 1-(2,6-dichlorobenzoyl)-3-(3,4-dichlorophenyl)-urea (DU 19,111), 1-(2,6-dichlorobenzoyl)-3-(4-chlorophenyl)-urea (pH 60-38), 1-(2,6-difluorobenzoyl)-3-(4-chlorophenyl)-urea (pH 60-40), N-2-methyl-4-chlorophenyl-N′,N′-dimethyl-thiourea and carbamates such as 2-methylthio-O-(N-methyl-carbamoyl)butanone-3-oxime (Butocarboxim)=Blumi, (2-ethylmercaptomethylphenyl)-N-methylcarbamate (Ethiophencarb), 1-dimethylcarbamoyl)-N-(methylcarbamoyloxy)-thioformhydroximic acid methyl ester (Oxamyl)=Vydate, 2,2-dimethyl-1,3-benzodioxol-4-yl-N-methylcarbamate (Bendoxicarb), 1-naphthyl-N-methyl-carbmate (Carbaryl), 4-dimethylamino-3,5-xylyl-N-methyl-carbamate, 4-dimethylamino-3-tolyl-N-methyl-carbamate (Aminocarb), 4-methylthio-3,5-xylyl-N-methylcarbamate (Methiocarb), 3,4,5-trimethylphenyl-N-methylcarbamate, 2-chlorophenyl-N-methylcarbamate (CPMC), 5-chloro-6-oxo-2-norbornane-carbonitrile-O-(methylcarbamoyl)-oxime, 1-(dimethylcarbamoyl)-5-methyl-3-pyrazolyl-N,N-dimethylcarbamate (Dimetilan), 2,3-dihydro-2,2-dimethyl-7-benzofuranyl-N-methylcarbamate (Carbofuran), 2-methyl-2-methylthio-propionaldehyde-O-(methylcarbamoyl)-oxime (Aldecarb), N-(1-ethylpropyl)phenyl-N-methylcarbamate, 3,5,di-tert.-butyl-N-methylcarbamate, N-(1-methylbutyl)phenyl-N-methylcarbamate, 2-isopropylphenyl-N-methylcarbamate (Isoprocarb), 2-sec.-butylphenyl-N-methylcarbamate, 3-isopropyl-5-methylphenyl-N-methylcarbamate (Promecarb), 2-(1,3-dioxolan-2-yl)phenyl-N-methylcarbamate (Dioxacarb), 2-isopropoxyphenyl-N-methylcarbamate (Arprocarb), 4-diallylamino)-3,5-xylyl-N-methylcarbamate (Allyxicarb), 2,3-dihydro-2-methyl-7-benzofuranyl-N-methylcarbamate (Decarbofuran), 1-isopropyl-3-methylpyrazol-5-yl-N,N-dimethylcarbamate (Isolan), 2-dimethylamino-5,6-dimethylpyrimidin-4-yl-N,N-dimethylcarbamate (Pirimicarb), 3,4-dimethylphenyl-N-methylcarbamate, 3-dimethylamino-methylene-iminophenyl-N-methylcarbamate (Formetanate) and its salts, 1-methylthioethyl-imino-N-methylcarbamate (Methomyl), 1,3-bis-(carbamoylthio)-2-(N,N-dimethylamino)-propane hydrochloride, 5,5-dimethylhydroresorcinol dimethylcarbamate and chlorinated hydrocarbons such as 6,7,8,9,10,10-hexachloro-1,5,5a,6,9,9a-hexahydro-6,9-methane, 2,3,4-benzodioxathiepine-3-oxide (Endosulfan), chlorinated camphene containing 67–69% of chlorine (Toxaphen), chlorinated terpenes (Strobane), 1,2,3,5,6,7,8,9,10,10-decachloro-pentacyclo-[5.2.1.0$^{2.6}$.0$^{3.9}$0$^{5.8}$]-decan-4-one (Chlordecone), dodecachlorooctahydro-1,3,4-metheno-2H-cyclobuta-(cd)-pentalene (Mirex), decachlorobi-2,4-cyclopentadiene-1-yl (Dekaflor), ethyl-1,1a3,3a,4,5,5a,5b,6-decachlorooctahydro-2-hydroxy-1,3,4-metheno-(2H)-cyclobuta[cd]pentalene-2-laevulinate (Lelevan), γ-hexachlorocyclohexane (Gammexane; Lindan; γHCH), 1,2,4,5,6,7,8,8-octachloro-3a,4,7,7a′tetrahydro-4,7-methylene-indane (Chlordan), 1,4,5,6,7,8,8-heptachloro, 3a,4,7,7a-tetrahydro-4,7-methylene-indane (Heptachlor), and 1,2,3,4,10,10-hexachloro-6,7-epoxy-1,4,4a,5,6,7,8,8a-octahydroendo-endo-5,8-dimethanonaphthalene (Endrin), as well as pheromones, synergistic agents, repellents, plant active compounds, metabolism products of micro-organisms and development inhibitors.

When high concentrations are used, the compounds according to the invention also exhibit a certain herbicidal action.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, peferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods, which comprises applying to at least one of correspondingly (a) such arthropods and (b) the corresponding habitat thereof, i.e. the locus to be protected, e.g. to a growing crop, to an area where a crop is to be grown or to a domestic animal, a correspondingly combative or toxic amount, i.e. an arthropodicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

When used against pests harmful to health and pests of stored products, the active compounds are distinguished by an excellent residual activity on wood and clay as well as a good stability to alkali on limed substrates.

The preparation of the new compounds of the present invention is illustrated, without limitation, by the following examples:

EXAMPLE 1

Process for the preparation of 1,3-bis-3'-trifluoromethylphenyl-triazine-2,4-dione 39.9 g (0.2 mol) of bis-trimethylsilyl-formamide were added dropwise to 74.8 g (0.4 mol) of 3-trifluoromethylphenyl isocyanate in 50 ml of ether sufficiently rapidly that the solvent just boiled. After completion of the reaction, ascertainable by the temperature rise, due to the strongly exothermic reaction, subsiding, the solvent as well as the hexamethyldisiloxane formed in the reaction were distilled off. The crystals which remained were recrystallized from ethanol. 72.4 g (90% of theory) of 1,3-bis-3'-trifluoromethylphenyl-triazine-2,4-dione of melting point 221° C. were obtained.

The following compounds were prepared analogously:

Table 1

| Compound No. | R | $R^1$ | Melting point °C. | Yield % |
|---|---|---|---|---|
| 2 | 2-Cl, 3-CF$_3$-phenyl | H | 225 | 64 |
| 3 | 4-(4-Cl-phenoxy)-phenyl | H | 174 | 79 |
| 4 | 3-(CH=CH-COOC$_2$H$_5$)-phenyl | H | 126 | 59 |
| 5 | 4-(H$_5$C$_2$O)-phenyl | H | 159 | 92 |

| Compound No | R | $R^1$ | Yield % |
|---|---|---|---|
| 6 | 4-(H$_5$C$_2$O)-phenyl | phenyl | 79 |
| 7 | 4-(4-Cl-phenoxy)-phenyl | C$_2$H$_5$ | 71 |
| 8 | " | i—C$_3$H$_7$ | 63 |
| 9 | " | n—C$_4$H$_9$ | 62 |
| 10 | " | phenyl | 68 |
| 11 | 3-F$_3$C-phenyl | C$_2$H$_5$ | 42 |
| 12 | " | i—C$_3$H$_7$ | 78 |
| 13 | " | n—C$_4$H$_9$ | 51 |
| 14 | " | phenyl | 63 |
| 15 | 2-Cl, 4-F$_3$C-phenyl | C$_2$H$_5$ | 90 |
| 16 | 2-Cl, 4-F$_3$C-phenyl | n—C$_4$H$_9$ | 48 |
| 17 | " | phenyl | 51 |
| 18 | 4-F$_3$C-phenyl | H | 67 |
| 19 | 4-(F$_3$C-S)-phenyl | H | 74 |
| 20 | 4-(F$_3$C-O)-phenyl | H | 58 |
| 21 | 4-(FClHC-F$_2$C-O)-phenyl | H | 66 |
| 22 | 4-(3-F$_3$C-phenoxy)-phenyl | H | 70 |
| 23 | Cl(CH$_2$)$_6$— | H | 98 |
| 24 | " | C$_2$H$_5$ | 95 |

Table 1-continued

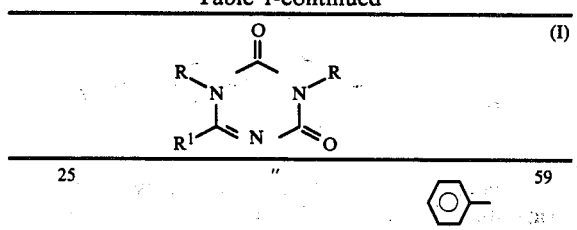

| | | | |
|---|---|---|---|
| 25 | " | ⌬— | 59 |

The experiments given below show the arthropod metamorphosis-inhibiting action of the compounds according to the invention without implying any limitation in respect of the breadth of action of these compounds. In these experiments, the morphological changes, such as half-pupated insects, incompletely slipped larvae or caterpillars, defective wings, pupal cuticula of imagos, and the mortality, are assessed throughout the entire stated development of the test insects.

EXAMPLE 2

Metamorphosis-inhibiting action/ingestion test

Test insects: *Plutella maculipennis* (caterpillars in the 4th stage of development)—20 insects *Phaedon cochleariae* (larvae in the 4th stage of development)—20 insects
Feed plants: Cabbage plants (*Brassica oleracea*)
Solvent: 10 parts by weight of dimethylformamide
Emulsifier: 1 part by weight of polyoxyethylene sorbitan monolaurate To produce a suitable preparation of active compound, 2 parts by weight of active compound were mixed with the stated amount of solvent and emulsifier and with sufficient water to give a 1% strength mixture, which was diluted with water to the desired concentration.

The test insects were fed with leaves of the feed plants, which were provided with a uniform spray coating of the active compound mixture of the chosen concentration, so that the required amounts of active compound in ppm (parts per million) were obtained on the leaves, until the imago developed.

As a control, leaves treated only with solvent and emulsifier of the appropriate concentration were used for feeding.

The active compounds according to the invention, obtained in the preparative examples, showed a good activity in this test.

EXAMPLE 3

Metamorphosis-inhibiting action/Laphygma test

Test insects: *Laphygma exigua* (caterpillars in the 4th stage of development)
Feed: 1 cm thick discs of 3 cm diameter of partially air-dried, synthetic feed of shredded beans, yeast, vitamin mixture, leaf powder, agar and preservative
Solvent: 10 parts by weight
Emulsifier: 1 part by weight of polyoxyethylene-20 sorbitan monolaurate To produce a suitable preparation of active compound, 2 parts by weight of active compound were mixed with the stated amount of solvent and emulsifier and sufficient water to give a 1% strength mixture, which was diluted with water to the desired concentration.

One test insect was placed on each of a number of feed discs, moistened with 1.5 ml of active compound solution of the desired concentration, so that the required concentration of active compound in ppm (parts per million), in the feed, was achieved, and the insect was observed until the imago slipped. 5 to 10 test insects were used per experiment.

As a control, one test insect was placed on each of a number of feed discs, moistened with 1.5 ml of solvent and emulsifier of the desired concentration, so that the required concentration in ppm (parts per million), in the feed, was achieved, and the insect was observed until the imago slipped.

The active compounds according to the invention, obtained in the preparative examples, showed a good activity in this test.

EXAMPLE 4

Metamorphosis-inhibiting action/yellow fever mosquito test

Test insects: *Aedes aegypti* (larvae in the 3rd stage of development); 20 insects
Solvent: 10 parts by weight
Emulsifier: 1 part by weight of polyoxyethylene-20-sorbitan monolaurate To produce a suitable preparation of active compound, 2 parts by weight of active compound were mixed with the stated amount of solvent and emulsifier and sufficient water to give a mixture containing 100 ppm of the active compound, which mixture was diluted with water to the desired concentration.

The test insects were placed in 90 ml of these active compound solutions and observed until the imago slipped. As a control, test insects were introduced into a solvent and emulsifier/water mixture of the required concentration and observed until the imago slipped.

The active compounds according to the invention, obtained in the preparative examples, showed a good activity in this test.

EXAMPLE 5

Development-inhibiting action/contact test

Test insects: *Dysdercus intermedius* (larvae in the 3rd stage of development); 10 insects
Feed: Cotton seeds (*Gossypium hirsutum*)
Solvent: 4 parts by weight of acetone
Emulsifier: 1 part by weight of alkylaryl polyglycol ether To produce a suitable preparation of active compound, 2 parts by weight of active compound were mixed with the stated amount of solvent and emulsifier and sufficient water to give a 1% strength mixture, which was diluted with water to the desired concentration.

The test insects were dipped for 3 seconds into the active compound mixture of the chosen concentration and then kept in cages and fed with untreated cotton seeds and water.

As a control, insects which had been dipped only in solvent and emulsifier were kept and fed in the same manner.

The active compounds according to the invention, obtained in the preparative examples, showed a good activity in this test.

It will be appreciated that the instant specification and examples are set forth by way of illustration and not limitation, and that various modifications and changes may be made without departing from the spirit and scope of the present invention.

What is claimed is:

1. A substituted triazine-2,4-dione of the formula

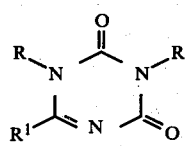

in which
R in both instances is identical and represents alkyl with up to 20 carbon atoms carrying one or more substituents selected from the group consisting of halogen, CN, aryloxy, alkoxy, halogenalkoxy, alkylmercapto, halogenalkylmercapto or represents furthermore phenyl carrying one or more substituents selected from the group consisting of halogenoalkyl, optionally halogen-substituted phenoxy, alkoxy, halogenoalkoxy, alkylmercapto, alkoxycarbonylalkenyl and halogenoalkylmercapto radicals and which can optionally be further substituted by halogen, or represents phenylsulphonyl which is optionally substituted by halogen, nitro, CN, monoalkylamino, dialkylamino, alkylmercapto or alkoxy, or represents alkylsulphonyl which is optionally substituted by halogen or CN, and
$R^1$ represents hydrogen or alkyl with 1–10 carbon atoms or cycloalkyl with 5–10 carbon atoms, either of which is optionally substituted by halogen, alkoxy, cyano or nitro, or represents phenyl or naphthyl which are optionally substituted by halogen, nitro, cyano, alkyl with 1–10 carbon atoms, halogenoalkyl, alkoxy or alkylmercapto.

2. A compound according to claim 1, in which R represents phenyl carrying one or more substitutents selected from the group of trihalogenomethyl, ethoxy, ethoxycarbonylvinyl, phenoxy and halogenophenoxy radicals and which can optionally be further substituted by chlorine, and $R^1$ represents hydrogen, methyl, ethyl, n-propyl, isopropyl, cyclohexyl or phenyl.

3. A compound according to claim 1, wherein such compound is 1,3-bis-3'-chloro-4'-trifluoromethylphenyl-triazine-2,4-dione of the formula

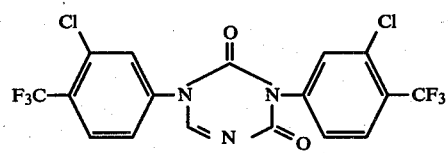

4. A compound according to claim 1, wherein such compound is 1,3-bis-4'-(4''-chlorophenoxy)-phenyl-triazine-2,4-dione of the formula

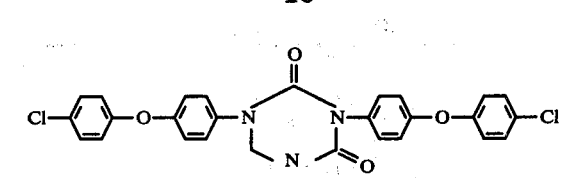

5. A compound according to claim 1, wherein such compound is 1,3-bis-4'-(4''-chlorophenoxy)-phenyl-6-isopropyl-triazine-2,4-dione of the formula

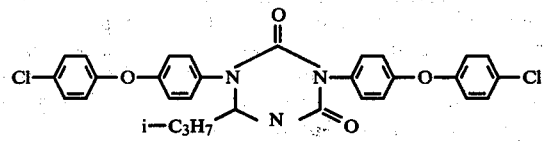

6. A compound according to claim 1, wherein such compound is 1,3-bis-3'-trifluoromethylphenyl-6-ethyl-triazine-2,4-dione of the formula

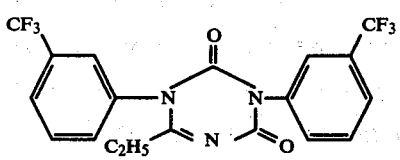

7. A compound according to claim 1, wherein such compound is 1,3-bis-3'-chloro-4'-trifluoromethylphenyl-6-n-butyl-triazine-2,4-dione of the formula

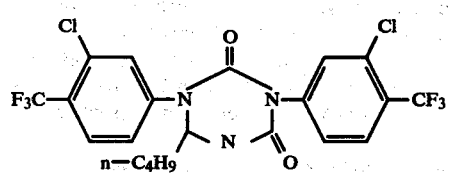

8. A process for the preparation of a compound according to claim 1, comprising reacting a bis-silylated carboxylic acid amide of the formula

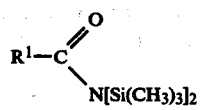

with an isocyanate of the formula

R—N=C=O.

9. A process according to claim 8, in which the reactants are employed in approximately stoichiometric amounts and the reaction is effected in an inert organic solvent at about 10° to 150° C.